US008540631B2

(12) United States Patent
Penner et al.

(10) Patent No.: US 8,540,631 B2
(45) Date of Patent: Sep. 24, 2013

(54) APPARATUS AND METHODS USING ACOUSTIC TELEMETRY FOR INTRABODY COMMUNICATIONS

(75) Inventors: Avi Penner, Tel Aviv (IL); Eyal Doron, Kiryat Yam (IL)

(73) Assignee: Remon Medical Technologies, Ltd., Caesarea (IL)

(*) Notice: Subject to any disclaimer, the term of this patent is extended or adjusted under 35 U.S.C. 154(b) by 1560 days.

(21) Appl. No.: 11/680,529

(22) Filed: Feb. 28, 2007

(65) Prior Publication Data
US 2007/0142728 A1   Jun. 21, 2007

Related U.S. Application Data

(63) Continuation of application No. 10/413,428, filed on Apr. 14, 2003, now Pat. No. 7,198,603.

(51) Int. Cl.
*A61B 5/07* (2006.01)
*A61B 5/02* (2006.01)

(52) U.S. Cl.
USPC ........... 600/302; 600/488; 600/486; 600/485; 600/481

(58) Field of Classification Search
USPC .................... 600/488, 481, 483–486, 302
See application file for complete search history.

(56) References Cited

U.S. PATENT DOCUMENTS

| 3,672,352 A | 6/1972 | Summers |
| 4,361,153 A | 11/1982 | Slocum et al. |
| 4,373,527 A | 2/1983 | Fischell |
| 4,481,950 A | 11/1984 | Duggan |
| 4,519,401 A | 5/1985 | Ko et al. |
| 4,573,994 A | 3/1986 | Fischell et al. |
| 4,614,192 A | 9/1986 | Imran et al. |
| 4,616,640 A | 10/1986 | Kaali et al. |
| 4,651,740 A | 3/1987 | Schroppel |
| 4,793,825 A | 12/1988 | Benjamin et al. |
| 5,113,859 A | 5/1992 | Funke |
| 5,423,334 A | 6/1995 | Jordan |
| 5,713,939 A | 2/1998 | Nedungadi et al. |

(Continued)

FOREIGN PATENT DOCUMENTS

| EP | 0300552 | 1/1989 |
| JP | 03-034196 | 2/1991 |

(Continued)

OTHER PUBLICATIONS

International Search Report and Written Opinion of international patent application No. PCT/IB2004/001046, mailed Aug. 25, 2004, 11 pp.

*Primary Examiner* — Navin Natnithithadha
(74) *Attorney, Agent, or Firm* — Faegre Baker Daniels LLP

(57) ABSTRACT

Systems and methods provide intrabody communication using acoustic telemetry. The system includes a first or control implant including a first acoustic transducer, and a second implant including a switch and a second acoustic transducer coupled to the switch. The second acoustic transducer receives acoustic signals from the first acoustic transducer for closing the switch to activate the second implant. The second implant may include a sensor for measuring a physiological parameter that is transmitted using acoustic signals including the physiological data to the first implant. For example, the second implant may measure pressure in the patient's heart that may be used by the first implant to control a pacemaker. Alternatively, the second implant may blood sugar concentration that may be used by the first implant to control an insulin pump. Alternatively, the first implant may store and transfer the data to an external device for monitoring the patient.

12 Claims, 5 Drawing Sheets

(56) References Cited

U.S. PATENT DOCUMENTS

| | | |
|---|---|---|
| 5,733,313 A | 3/1998 | Barreras, Sr. et al. |
| 5,778,882 A | 7/1998 | Raymond et al. |
| 5,800,478 A | 9/1998 | Chen et al. |
| 5,814,089 A | 9/1998 | Stokes et al. |
| 5,833,603 A | 11/1998 | Kovacs et al. |
| 6,140,740 A | 10/2000 | Porat et al. |
| 6,141,588 A | 10/2000 | Cox et al. |
| 6,162,238 A | 12/2000 | Kaplan et al. |
| 6,164,284 A | 12/2000 | Schulman et al. |
| 6,170,488 B1 | 1/2001 | Spillman, Jr. et al. |
| 6,185,452 B1 | 2/2001 | Schulman et al. |
| 6,200,265 B1 | 3/2001 | Walsh et al. |
| 6,234,973 B1 | 5/2001 | Meador et al. |
| 6,236,889 B1 | 5/2001 | Soykan et al. |
| 6,277,078 B1 | 8/2001 | Porat et al. |
| 6,308,099 B1 | 10/2001 | Fox et al. |
| 6,336,903 B1 | 1/2002 | Bardy |
| 6,368,284 B1 | 4/2002 | Bardy |
| 6,398,728 B1 | 6/2002 | Bardy |
| 6,411,840 B1 | 6/2002 | Bardy |
| 6,431,175 B1 | 8/2002 | Penner et al. |
| 6,440,066 B1 | 8/2002 | Bardy |
| 6,442,413 B1 | 8/2002 | Silver |
| 6,442,433 B1 | 8/2002 | Linberg |
| 6,445,953 B1 | 9/2002 | Bulkes et al. |
| 6,453,196 B1 | 9/2002 | Von Arx et al. |
| 6,456,602 B1 | 9/2002 | Hwang et al. |
| 6,456,883 B1 | 9/2002 | Torgerson et al. |
| 6,472,991 B1 | 10/2002 | Schulman et al. |
| 6,628,989 B1 | 9/2003 | Penner et al. |
| 6,638,231 B2 | 10/2003 | Govari et al. |
| 6,654,638 B1 | 11/2003 | Sweeney |
| 6,675,049 B2 | 1/2004 | Thompson et al. |
| 6,712,772 B2 | 3/2004 | Cohen et al. |
| 6,764,446 B2 | 7/2004 | Wolinksy et al. |
| 6,783,499 B2 | 8/2004 | Schwartz |
| 6,792,311 B2 | 9/2004 | Fox et al. |
| 6,809,507 B2 | 10/2004 | Morgan et al. |
| 6,823,031 B1 | 11/2004 | Tatem, Jr. |
| 6,840,956 B1 | 1/2005 | Wolinsky et al. |
| 6,855,115 B2 | 2/2005 | Fonseca et al. |
| 6,895,265 B2 | 5/2005 | Silver |
| 6,907,285 B2 | 6/2005 | Denker et al. |
| 6,978,182 B2 | 12/2005 | Mazar et al. |
| 6,985,773 B2 | 1/2006 | Von Arx et al. |
| 7,003,350 B2 | 2/2006 | Denker et al. |
| 7,018,336 B2 | 3/2006 | Enegren et al. |
| 7,024,428 B1 | 4/2006 | Huang et al. |
| 7,027,871 B2 | 4/2006 | Burnes et al. |
| 7,033,322 B2 | 4/2006 | Silver |
| 7,061,381 B2 | 6/2006 | Forcier et al. |
| 7,134,999 B2 | 11/2006 | Brauker et al. |
| 7,187,979 B2 | 3/2007 | Haubrich et al. |
| 7,198,603 B2 | 4/2007 | Penner et al. |
| 7,214,189 B2 | 5/2007 | Zdeblick |
| 7,236,821 B2 | 6/2007 | Cates et al. |
| 7,273,454 B2 | 9/2007 | Raymond et al. |
| 7,273,457 B2 | 9/2007 | Penner |
| 7,399,313 B2 | 7/2008 | Brown et al. |
| 7,425,200 B2 | 9/2008 | Brockway et al. |
| 7,452,334 B2 | 11/2008 | Gianchandani et al. |
| 7,481,771 B2 | 1/2009 | Fonseca et al. |
| 2001/0043514 A1 | 11/2001 | Kita |
| 2002/0042561 A1 | 4/2002 | Schulman et al. |
| 2002/0045812 A1 | 4/2002 | Ben-Haim et al. |
| 2002/0065540 A1 | 5/2002 | Lebel et al. |
| 2002/0077673 A1 | 6/2002 | Penner et al. |
| 2002/0151770 A1 | 10/2002 | Noll, III et al. |
| 2002/0177782 A1 | 11/2002 | Penner |
| 2002/0183628 A1 | 12/2002 | Reich et al. |
| 2003/0009204 A1 | 1/2003 | Amundson |
| 2003/0136417 A1 | 7/2003 | Fonseca et al. |
| 2003/0181794 A1 | 9/2003 | Rini et al. |
| 2003/0191383 A1 | 10/2003 | Ben-Haim et al. |
| 2003/0195581 A1 | 10/2003 | Meadows et al. |
| 2004/0057340 A1 | 3/2004 | Charles-Erickson et al. |
| 2004/0064133 A1 | 4/2004 | Miller et al. |
| 2004/0088009 A1 | 5/2004 | Degroot |
| 2004/0152999 A1 | 8/2004 | Cohen et al. |
| 2005/0056539 A1 | 3/2005 | Morgan et al. |
| 2005/0159789 A1 | 7/2005 | Brockway et al. |
| 2005/0187482 A1 | 8/2005 | O'Brien et al. |
| 2005/0215887 A1 | 9/2005 | Ben-Haim et al. |
| 2005/0242479 A1 | 11/2005 | Petisce et al. |
| 2006/0004263 A1 | 1/2006 | Feliss et al. |
| 2006/0009818 A1 | 1/2006 | Von Arx et al. |
| 2006/0030903 A1 | 2/2006 | Seeberger et al. |
| 2006/0031378 A1 | 2/2006 | Vallapureddy et al. |
| 2006/0085039 A1 | 4/2006 | Hastings et al. |
| 2006/0085041 A1 | 4/2006 | Hastings et al. |
| 2006/0085042 A1 | 4/2006 | Hastings et al. |
| 2006/0122667 A1 | 6/2006 | Chavan et al. |
| 2006/0136004 A1 | 6/2006 | Cowan et al. |
| 2007/0053513 A1 | 3/2007 | Hoffberg |
| 2007/0208261 A1 | 9/2007 | Maniak et al. |
| 2008/0021333 A1 | 1/2008 | Huelskamp |
| 2008/0021972 A1 | 1/2008 | Huelskamp et al. |
| 2008/0082146 A1 | 4/2008 | Gandhi et al. |
| 2008/0112885 A1 | 5/2008 | Okunev et al. |
| 2008/0114224 A1 | 5/2008 | Brandy |
| 2008/0129457 A1 | 6/2008 | Ritter et al. |
| 2008/0191581 A9 | 8/2008 | Penner et al. |
| 2008/0288038 A1 | 11/2008 | Paul et al. |
| 2008/0294208 A1 | 11/2008 | Willis et al. |
| 2008/0312719 A1 | 12/2008 | Keilman |
| 2009/0074216 A1 | 3/2009 | Bradford et al. |
| 2009/0075687 A1 | 3/2009 | Hino et al. |
| 2009/0177251 A1 | 7/2009 | Huelskamp et al. |
| 2009/0198307 A1 | 8/2009 | Mi et al. |
| 2010/0042177 A1 | 2/2010 | Stahmann et al. |

FOREIGN PATENT DOCUMENTS

| | | |
|---|---|---|
| JP | 10-055202 | 2/1998 |
| JP | 2008-505714 | 2/2008 |
| WO | 9934453 | 7/1999 |
| WO | 9934731 | 7/1999 |
| WO | WO2004/089465 | 10/2004 |
| WO | WO2006/045073 | 4/2006 |
| WO | WO2006/045074 | 4/2006 |
| WO | WO2006/045075 | 4/2006 |
| WO | WO2006/069215 | 6/2006 |
| WO | 2007/070794 | 6/2007 |
| WO | WO2008/011592 | 1/2008 |
| WO | WO2008/011593 | 1/2008 |
| WO | WO 2008/060197 | 5/2008 |
| WO | 2009102640 A1 | 8/2009 |

APPARATUS AND METHODS USING ACOUSTIC TELEMETRY FOR INTRABODY COMMUNICATIONS

This application is a continuation of application Ser. No. 10/413,428, filed Apr. 14, 2003, now U.S. Pat. No. 7,198,603.

INTRODUCTION

The present invention relates generally to devices for implantation within a patient's body, and more particularly to systems and methods for communication within a patient's body using acoustic telemetry, e.g., using one implant within a body to activate, deactivate, and/or otherwise control one or more additional implants located within the body that monitor physiological conditions and/or provide therapeutic functions.

BACKGROUND OF THE INVENTION

Devices are known that may be implanted within a patient's body to monitor one or more physiological conditions and/or to provide therapeutic functions. For example, sensors or transducers may be located deep within the body for monitoring a variety of properties, such as temperature, pressure, strain, fluid flow, chemical properties, electrical properties, magnetic properties, and the like. In addition, devices may be implanted that perform one or more therapeutic functions, such as drug delivery, defibrillation, electrical stimulation, and the like.

Often it is desirable to control or otherwise communicate with such devices once they are implanted within a patient, for example, to obtain data, and/or to activate or deactivate the implanted device. An implant may include wire leads that extend from the implant to an exterior surface of the patient, thereby allowing an external controller or other device to be directly coupled to the implant. Alternatively, the implant may be remotely controlled or communicated with using an external induction device. For example, an external radio frequency (RF) transmitter may be used to communicate with the implant. In addition, RF devices have been suggested that may be implanted within a patient's body to communicate with another implant at another location within the patient's body.

RF energy, however, may only penetrate a few millimeters within a body, because of the body's dielectric nature, and therefore may not be able to communicate effectively with an implant that is located deep within the body. RF devices may also require substantial electrical power, because the devices generally consume electrical energy even when in a dormant state. In addition, although an RF transmitter may be able to induce a current within an implant, the implant's receiving antenna, generally a low impedance coil, may generate a voltage that is too low to provide a reliable switching mechanism.

In a further alternative, magnetic energy may be used to control or otherwise communicate with an implant, since a body generally does not attenuate magnetic fields. The presence of external magnetic fields encountered by the patient during normal activity, however, may expose the patient to the risk of false positives, i.e., accidental activation or deactivation of the implant. Furthermore, external electromagnetic systems may be cumbersome and may not be able to effectively transfer coded information to an implant.

Accordingly, it is believed that apparatus and methods for communicating with implants using acoustic telemetry would be useful.

SUMMARY OF THE INVENTION

The present invention is generally directed to implants that may be surgically or otherwise located within a body for monitoring one or more physiological parameters and/or for performing one or more therapeutic functions. More particularly, the present invention is directed to systems and methods for communicating between implants within a patient's body using acoustic telemetry, e.g., using one implant within the body to activate, deactivate, and/or otherwise control another implant located within the body. One or both of the implants may monitor physiological conditions and/or provide therapeutic functions. Implants in accordance with the present invention may be used for various diagnostic and/or therapeutic functions, e.g., atrial defibrillation, pacing, pain relief stimulation, neuro-stimulation, drug release, activation of a light source for photodynamic therapy, monitoring of a radiation dose including ionizing, magnetic or acoustic radiation, monitoring of flow in a bypass graft, producing cell oxygenation and membrane electroporation, and measurement of various physiological parameters including heart chamber pressure, infraction temperature, intracranial pressure, electrical impedance, position, orthopedic implant strain/displacement, or pH.

In a accordance with a first aspect of the present invention, a system is provided for communication within a patient's body that includes a first implant, also called a control implant and a second implant, also called a dormant implant. Optionally, the system may include one or more additional implants, e.g., one or more additional dormant implants, and/or the system may include a therapeutic device for treating the patient.

Generally, the first implant includes a first acoustic transducer for transmitting acoustic signals. The first implant may include other components, e.g., a processor, controller, and/or other electrical circuitry, memory, an energy source (e.g., a nonrechargeable or rechargeable battery and/or capacitor), one or more sensors, and/or a therapeutic device. The second implant generally includes an electrical circuit configured for performing one or more commands when the implant is activated; a switch coupled to the electrical circuit; and a second acoustic transducer coupled to the switch, the acoustic transducer configured for receiving one or more acoustic signals from the first acoustic transducer for closing the switch to activate the second implant.

Preferably, the switch is configured such that the switch is closed only when the second acoustic transducer receives a first acoustic excitation signal followed by a second acoustic excitation signal, the first and second acoustic excitation signals being separated by a predetermined delay. This or other signal configurations may be used, e.g., when it is desired to activate one of a plurality of available dormant implants controlled by the first implant.

In a first preferred embodiment, the second implant may include a sensor coupled to the electrical circuit, the sensor configured for measuring a physiological parameter within the body when the second implant is activated. The second acoustic transducer may be configured for transmitting a signal including physiological data related to the measured physiological parameter to the first acoustic transducer.

For example, the first implant may include a controller coupled to a pacemaker, and the second implant may include a pressure sensor for measuring pressure in the patient's heart. The second implant may be configured to transmit acoustic signals to the first implant, the acoustic signals including the measured pressure within the patient's heart. The controller may be configured for extracting the measured pressure from the acoustic signals and controlling the pacemaker at least partially based upon the measured pressure.

In another example, the first implant may include a controller coupled to an insulin pump, and the second implant may include a glucose sensor for measuring blood sugar concentration within the patient's body. The second implant may be configured to transmit acoustic signals to the first implant, the acoustic signals including measured blood sugar concentration within the patient's body. The controller may be configured for extracting the measured blood sugar concentration from the acoustic signals and controlling the insulin pump at least partially based upon the measured blood sugar concentration.

In yet another example, the second implant may include a sensor for measuring a physiological parameter within the patient's body. The second implant may be configured to transmit acoustic signals to the first implant, the acoustic signals including data related to the measured physiological parameter. The first implant may include memory for storing the data related to the measured physiological parameter, and a transmitter for transmitting the data to a device located outside the patient's body.

In accordance with another aspect of the present invention, a method is provided for communicating between first and second implants implanted at different locations within a patient's body, the second implant including an acoustic switch coupled to an electrical circuit. An acoustic activation signal may be transmitted from the first implant towards the second implant; and the acoustic switch may be closed in response to the acoustic activation signal, whereupon the second implant becomes activated.

Once activated, the second implant may measure a physiological parameter within the body, e.g., blood pressure within a chamber or other vessel of the patient's heart, or in a peripheral vessel, such as the aorta, renal, or iliac artery. Alternatively, the second implant may measure blood sugar concentration. The second implant may transmit an acoustic signal including data related to the physiological parameter from the second implant towards the first implant.

The first implant may store the data related to the physiological parameter in memory of the first implant, e.g., along with a time stamp identifying when the parameter was measured for later retrieval. For example, an external device outside the patient's body may interrogate the first implant, whereupon the first implant may transmit one or more acoustic or electromagnetic signals including the data related to the physiological parameter. In addition or alternatively, the first implant may control a therapeutic device, e.g., an insulin pump, pacemaker, and the like, at least partially based upon the data related to the physiological parameter.

In accordance with yet another aspect of the present invention, a method is provided for monitoring a physiological parameter within a patient's body. One or more acoustic signals are transmitted from a control implant implanted within the body to activate a dormant implant located at a location within the body. A physiological parameter is measured at the location with the dormant implant, and one or more acoustic signals are transmitted from the dormant implant to the control implant, the one or more acoustic signals including the physiological parameter data measured by the dormant implant.

In one embodiment, the control implant may store the data in memory. Optionally, the control implant may activate a plurality of dormant implants located within the body, whereupon each of the dormant implants may measure a physiological parameter and transmit one or more acoustic signals to the control implant, the one or more acoustic signals including physiological parameter data measured by each respective dormant implant. Subsequently, the control implant may be interrogated using an external device disposed outside the body, whereupon the control implant may transmit data including the physiological parameter data (from one or more dormant implants if multiple dormant implants are present) to the external device, e.g., using acoustic or RF telemetry.

For example, the dormant implant(s) may measure pressure, e.g., within the patient's aorta, a renal or iliac artery, and the like. The pressure data may be transmitted by the control implant to an external device such that the data may be used by a healthcare professional to monitor a condition of the patient.

In another embodiment, the patient's heart may be electrically stimulated based at least in part upon the pressure data measured by the dormant implant. For example, the dormant implant may be implanted within a chamber of the heart or a pulmonary artery. The control implant may be included in a pacemaker or coupled to a pacemaker for controlling the pacing provided by the pacemaker.

In yet another embodiment, the dormant implant may measure blood sugar concentration at a location within the patient's body, and transmit one or more acoustic signals to the control implant, the one or more acoustic signals including blood sugar concentration data measured by the dormant implant. Insulin may be delivered into the body based at least in part upon the blood sugar concentration measured by the dormant implant, e.g., using an insulin pump coupled to the control implant or including the implant therein.

Thus, the systems and methods of the present invention may facilitate intrabody communication between two implants using acoustic telemetry, where one of the implants may serve as a master implant, controlling the operation of the second (or additional) implant. The first implant, via an acoustic command, may switch the second passive implant to an active status, whereupon it may perform a series of predefined activities including therapeutic and/or diagnostic functions. At any stage of its operation, the second implant may communicate with the first implant, i.e., transmitting and/or receiving information. For example, the second implant may activate drugs using photodynamic therapy or ultrasonic activation or control opening of a drug reservoir.

Via the communication bus, the second implant may receive commands, e.g., related to dosing or other parameters that may be preprogrammed, externally controlled, or provide feedback from a sensor that monitor some relevant physiological parameter. A sensor may be included in either implant or in a third implant, e.g., in communication with the first implant. Alternatively, the second implant may serve as a sensor for some physiological or physical parameter, including pressure, blood coagulation, acidity level (pH), temperature, flow, impedance, glucose, potassium, calcium, light attenuation, acceleration, oxygen saturation, drug concentrations, and the like.

Other objects and features of the present invention will become apparent from consideration of the following description taken in conjunction with the accompanying drawings.

BRIEF DESCRIPTION OF THE DRAWINGS

The invention is herein described, by way of example only, with reference to the accompanying drawings, wherein.

DESCRIPTION OF THE PREFERRED EMBODIMENTS

Figure 1:
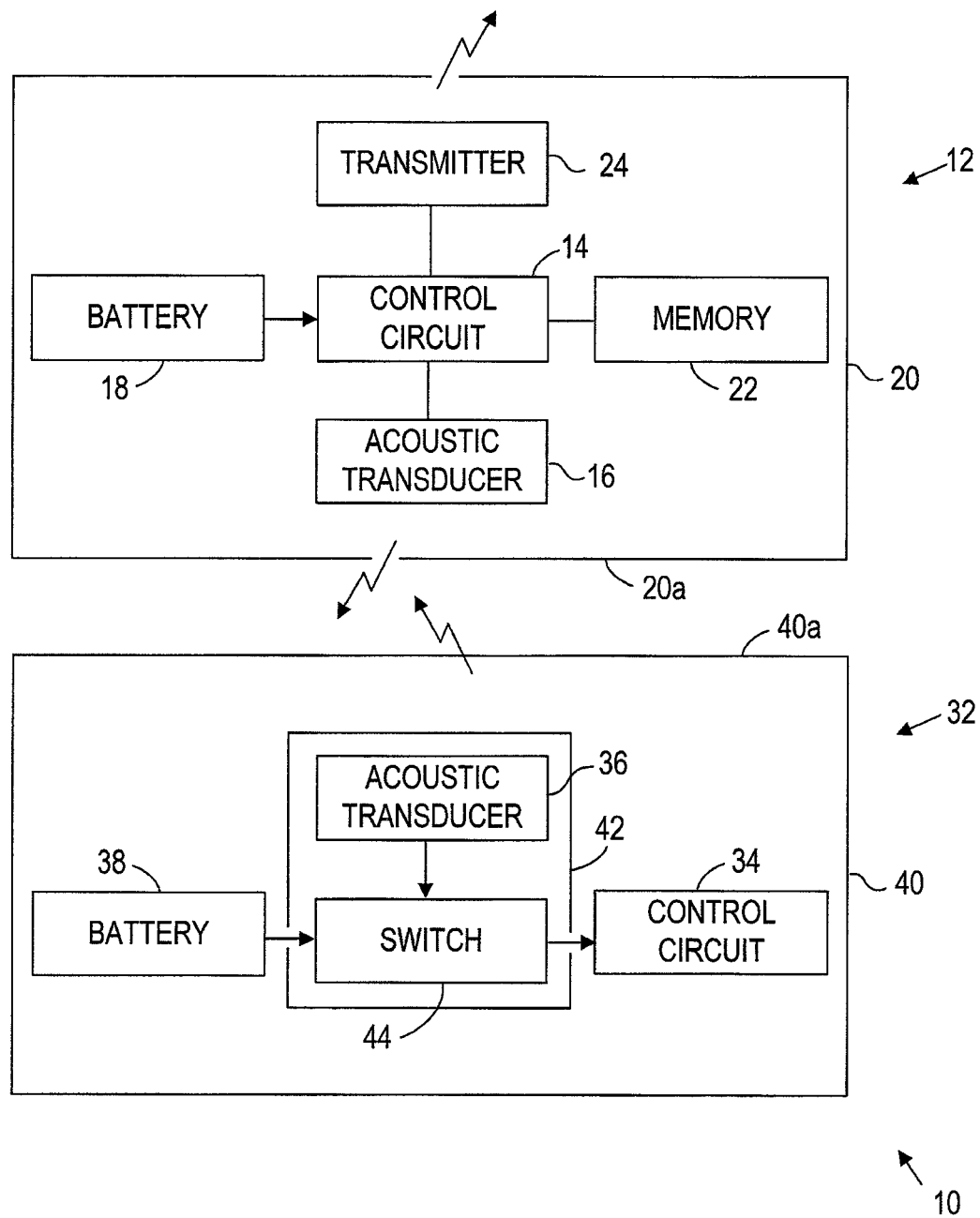
FIG. 1 is a block diagram, showing an exemplary embodiment of a system including two implants that may communicate with one another using acoustic telemetry, in accordance with the present invention.

Turning to the drawings, FIG. 1 shows a first preferred embodiment of a system 10 for intrabody communication between two or more implants implanted within a patient's body (not shown). Generally, the system 10 includes a first implant 12 (also called the control or master implant), and a second implant 32 (also called the dormant or slave implant). Optionally, the system 10 may include additional implants (not shown), e.g., one or more additional dormant or slave implants, similar to the second implant 32, with which the control implant 12 may communicate, as described below.

I. Control Implant

The control implant 12 may include a plurality of components, e.g., electrical circuitry 14, an acoustic transducer 16, and/or an energy source 18, provided within a box or casing 20. The casing 20, e.g., formed from titanium and the like, may be substantially sealed, and preferably hermetically sealed to substantially isolate the components of the control implant 12 from outside the casing 20. The casing 20 may include one or more regions, e.g., one or more side panels, that facilitate acoustic energy passing through the casing 20, i.e., to and/or from the acoustic transducer 16. For example a panel 20a overlying the acoustic transducer 16 may be a relatively thin wall of titanium or other material, e.g., having a thickness of about one half millimeter (0.5 mm) or less, that may allow acoustic waves to pass substantially therethrough. Additional information on possible ways to construct any of the implants discussed herein may be found in co-pending application Ser. No. 09/888,272, filed Jun. 21, 2001, the disclosure of which is expressly incorporated herein by reference.

The electrical circuitry 14 may be coupled to the energy source 18 such that at least some component(s) of the electrical circuitry 14 may remain active at all times, although, alternatively, all or part of the electrical circuitry 14 may be periodically dormant and/or selectively activated. The electrical circuitry 14 may include one or more controllers for controlling components of the control implant 12, timer circuitry (e.g., a clock or counter), an oscillator or other circuitry for driving the first acoustic transducer 16, and/or a processor for generating electrical signals being transmitted by and/or analyzing electrical signals received by the first acoustic transducer 16 (not shown).

In addition, the control implant 12 may include memory 22, e.g., volatile or non-volatile memory, including flash memory or ferroelectric memory. The memory 22 may store information, e.g., data received from one or more sensors (not shown) of the control implant 12 and/or the dormant implant 32, and/or commands for use internally or for controlling the dormant implant 32. Optionally, the control implant 12 may include a transmitter and/or receiver 24 for communicating with external devices (not shown), e.g., a radio frequency ("RF") or acoustic transmitter and/or receiver. The circuitry 14 of the control implant 12 may include one or more microcontrollers, digital signal processors ("DSPs"), Field Programmable Gate Arrays ("FPGAs"), other programmable devices, and/or any other hardware components or software modules that may be required for processing, analyzing, and/or storing data and/or for controlling operation of the control implant 12 and/or dormant implant(s) 32.

Optionally, the control implant 12 may include an acoustic switch (not shown) for activating and/or deactivated the control implant 12 during use. In addition or alternatively, the control implant 12 may include one or more sensors (not shown) for measuring or otherwise monitoring one or more physiological parameters, similar to the dormant implant 32, as described further below. In addition or alternative, the control implant 12 may include an actuator (not shown) for actuating a therapeutic and/or diagnostic device coupled to the control implant 12. Examples of implants including acoustic switches, sensors, and/or actuators are disclosed in co-pending application Ser. No. 10/152,091, filed May 20, 2002, Ser. No. 09/989,912, filed Nov. 19, 2001, Ser. No. 09/888,272, filed Jun. 21, 2001, and Ser. No. 09/690,615, filed Oct. 16, 2000. The disclosures of these references and any others cited therein are expressly incorporated by reference herein.

The acoustic transducer 16 generally includes one or more piezoelectric elements (not shown) configured for transmitting one or more acoustic signals, e.g., including an activation or deactivation command, such that the acoustic signal(s) may reach the dormant implant 32. In addition, the acoustic transducer 16 may include one or more piezoelectric elements (also not shown) for receiving one or more acoustic signals, e.g., from the dormant implant(s) 32 and/or from an external device (not shown). It will be appreciated by those skilled in the art that the same or different piezoelectric elements may be used for transmitting and receiving acoustic signals.

The acoustic transducer 16 may transmit acoustic waves or signals intended to reach one or more dormant implants 32. For example, the acoustic signals may include one or more activation signals to activate one or more dormant implants, one or more deactivation signals, and/or commands to program or otherwise instruct the dormant implant(s), e.g., to follow or modify a sequence of operations performed by the dormant implant(s). In addition, the acoustic transducer 16 may be used to communicate with an external device, e.g., a controller or recorder (not shown), and/or to act as an energy exchanger, i.e., to receive acoustic or electromagnetic energy from an external charger that may be used to recharge the control implant 12.

Figure 2A:
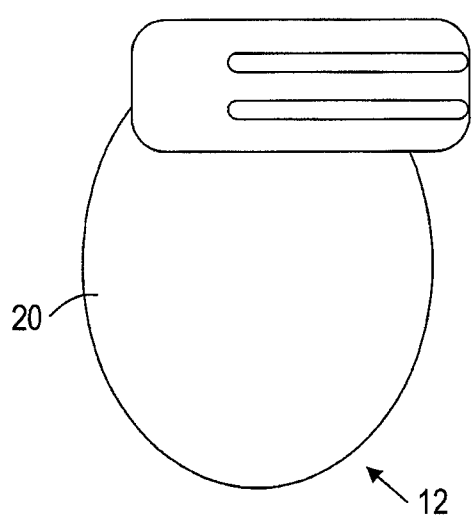
FIG. 2A is a top view of a first embodiment of a control implant, in accordance with the present invention.
Figure 2B:
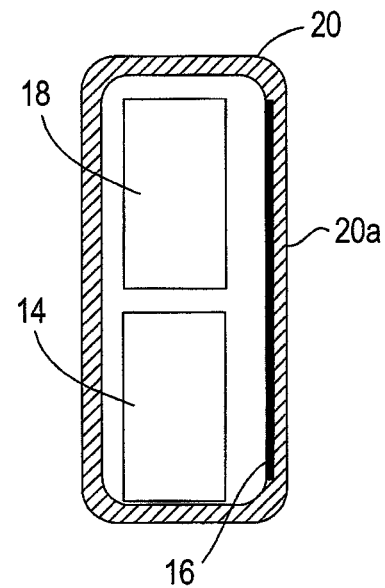
FIG. 2B is a cross-section of the control implant of FIG. 2A.
Figure 3:
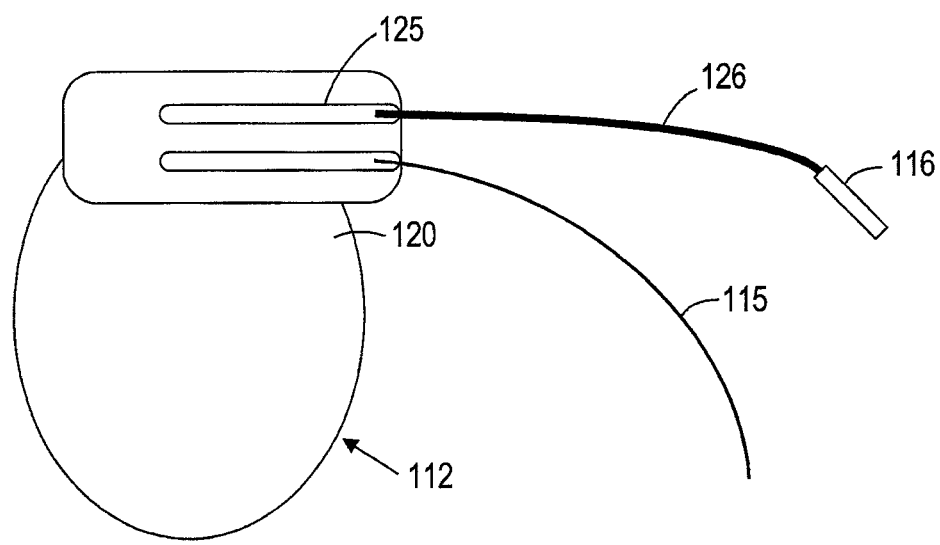
FIG. 3 is a top view of another embodiment of a control implant, in accordance with the present invention.

An exemplary embodiment of a control implant 12 is shown in FIGS. 2A and 2B that includes an acoustic transducer 16 integrated within a hermetically sealed casing 20. Another embodiment of a control implant 112 is shown in FIG. 3 in which the acoustic transducer 116 is a piezoelectric ceramic cylinder provided at the tip of a lead 126. This configuration may facilitate integrating the control implant 112 into an existing medical implant with minimal modifications, e.g., a pacemaker, because the acoustic transducer 116 may be attached to an outer surface of the casing 120 containing the components of the implant 112.

A. Exemplary Interrogation Energy Requirements

The following description illustrates exemplary energy consumption parameters, and, consequently, exemplary power requirements for an energy source, such as a battery, for a control implant, such as the control implant 12 shown in FIGS. 1, 2A, and 2B. Acoustic energy exchangers or transducers may currently achieve a sensitivity of about 2 V/kPa. An acoustic switch, which may be used to activate the implant, may operate by closing a MOSFET switch, which may require about a half volt (0.5 V) in silicon piezoelectric elements. The minimal acoustic level required to close the acoustic switch is therefore between about two hundred fifty and five hundred Pascals (250-500 Pa). Assuming a distance between transmitter and receiver (e.g., the distance between the acoustic transducers of control and dormant implants implanted within a patient's body) of about ten centimeters (10 cm), the acoustic power yielding five hundred Pascals (500 Pa @ 10 cm) is therefore:

$$P = 4\pi R^2 p^2 / (\rho c) = 21 \text{ mW} \quad (1)$$

where "$\rho$" and "$c$" are the density and sound velocity of water, respectively, "$R$" is the distance and "$p$" is the desired acoustic pressure. Assuming an electro-acoustic conversion efficiency of twenty percent (20%), this equation would provide an instantaneous electrical power requirement of about one hundred milliwatts (100 mW).

It may be possible to close the switch using only a single acoustic oscillation. However, this may not be practical, as it may require an extremely wideband transducer and matching network. A more realistic estimate may be a pulse length of between about five and ten (5-10) oscillations. A ten (10) oscillation pulse at forty kilohertz (40 kHz) is about two hundred fifty microseconds (250 μsec) long. Thus, the energy expended in such a pulse would be:

$$E = 250 \times 10^{-6} \times 0.1 = 25 \text{ μJ} \quad (2)$$

A typical interrogation would consist of between one and four pulses. Thus, for one interrogation per hour, the energy drain would be:

$$P = 25 \times 10^{-6} \times 4 / 3600 = 0.028 \text{ μW} \quad (3)$$

In addition, the power requirements of the receiver should be considered. An amplifier of the required sensitivity may take about ten milliWatts (10 mW) of power. If it is powered for one second every hour, this translates to a mean power drain of about 2.8 μW. This may be lowered by a factor of at least two to ten (2-10) by using more aggressive power management, e.g. by powering down the amplifier between words and/or focusing on specific segments of the pressure waveform such as the diastole. This power requirement may be substantially larger than the power taken by the transmission itself. Thus, the power drain of the interrogation circuits may be on the order of about one microwatt (1 μW).

B. Exemplary Transmitter/Receiver Element (Acoustic Transducer)

The acoustic transducer of a control implant ("the interrogating transducer") may be constructed in many ways. One example is a piezoelectric ceramic cylinder, identified in FIG. 3 as acoustic transducer 116. Such a product is sold by Physik Instrumente (PI) GmbH & Co. KG of Karlsruhe, Germany, and identified as PIC181 PZT. The cylinder inflates and contracts under the influence of an applied alternating voltage. This changes its volume and transmits an acoustic signal into any surrounding fluid as a simple (i.e., monopole) source.

The equation relating the acoustic output of a monopole source with its mechanical vibrations is:

$$p = \rho c / (2\lambda R) \times \partial V / \partial t \quad (4)$$

where "$\lambda$" is the acoustic wavelength and "$V$" is the element volume. To get the required acoustic level of 500 Pa @ 10 cm at 40 kHz, a volume change of about $2.5 \times 10^{-6}$ m$^3$/sec is needed, or a volume change amplitude of about $10^{-11}$ m$^3$.

Assume, for example, that the transmitter is a ceramic cylinder having a length of about ten millimeters (L=10 mm) and radius of about two and a half millimeters (a=2.5 mm), with electrodes on its inner and outer surfaces. Applying a voltage causes the material to expand equally in the tangential and axial directions, since the ceramic material is isotropic. The total volume change is then given by:

$$dV = dV/da \, da + dV/dL \, dL = 3VS \quad (5)$$

where "$S$" is the strain. To obtain a volume change of $10^{-11}$ m$^3$, a strain must be induced of about $4 \times 10^{-6}$. For the PIC181 PZT from PI, the piezoelectric strain constant is $120 \times 10^{-12}$ m/m/V/m. Thus, to obtain a strain of $4 \times 10^{-6}$, an electrical field of about 33,000 V/m should be applied, or an amplitude of about thirty three volts (33 V) for a wall thickness of about one millimeter (1 mm).

The battery to provide this energy may be one of a variety of types, such as those used in other active implantable devices, such as defibrillators, pacemakers, nerve stimulators, and the like. For example, the battery may be Lithium polymer, Lithium iodide, Lithium ion, and/or nickel metal. Assuming that the acoustic transducer may be used to activate the dormant implant every hour, the average power will be about one microwatt (1 μW), which is less than the power used by conventional pacemakers.

II. Dormant Implant

Returning to FIG. 1, an exemplary embodiment of a second or dormant implant 32 is shown. Generally, similar to the control implant 12, the dormant implant 32 may include a plurality of components, e.g., electrical circuitry 34, an acoustic switch 42, and/or an energy source 38, contained within a casing 40. The casing 40, e.g., formed from titanium and the like, may be hermetically or otherwise sealed to substantially isolate the components of the dormant implant 312 from outside the casing 40. The casing 40 may include one or more regions that facilitate acoustic energy passing through the casing 40. For example, a panel 40a overlying the acoustic transducer 36 may be a relatively thin membrane of titanium or other material, e.g., having a thickness of about fifty micrometers (50 μm) or less, that may allow acoustic waves to pass therethrough.

The acoustic switch 42 is coupled to the electrical circuitry 34 and the energy source 38, and may be activated upon acoustic excitation by an external acoustic energy source, e.g., from the control implant 12, to allow current flow from the energy source 38 to the electrical circuitry 34. In a preferred embodiment, the acoustic switch 42 includes an energy exchanger, i.e., an acoustic transducer 36, and a switch circuit 44. Exemplary switch circuits and acoustic switches that may be used with implants of the present invention are disclosed in co-pending application Ser. Nos. 10/152,091, 09/989,912, 09/888,272, and 09/690,615, incorporated by reference above. Basically, an acoustic transmission from the control implant 12 may vibrate the acoustic transducer 36 of the dormant implant 32, forming a voltage pulse that is conveyed to the switch circuit 44. When the voltage exceeds a predetermined threshold, e.g., about a half volt (0.5 V), the switch circuit 44 may close, and current may flow from the energy source 38, thereby activating the implant 32.

The energy source 38 may include any of a variety of devices, such as an energy exchanger, a battery, and/or a capacitor (not shown). Preferably, the energy source 38 is a battery capable of storing electrical energy substantially indefinitely, e.g., for as long as the acoustic switch 42 remains open, i.e., when the dormant implant 32 is in a "sleep" mode. In addition, the energy source 38 may be capable of being charged from an external source, e.g., inductively, using acoustic energy received by the acoustic transducer 36, as will be appreciated by those skilled in the art.

In another embodiment, the energy source 38 may include both a capacitor and a primary, non-rechargeable battery, although, alternatively, the energy source 38 may include a secondary, rechargeable battery and/or capacitor that may be energized before activation or use of the dormant implant 32. For example, the energy source 38 may include a Lithium thin film battery, such as those available from Oak Ridge Microenergy Inc. of Salt Lake City, Utah, Infinite Power Supply of Denver, Colo., or Cymber Corporation of Elk River, Minn. Alternatively, the energy source 38 may include a standard coin type manganese lithium rechargeable battery, such as those available from Matsushita Battery Industrial Co., Ltd. (MBI) of Osaka, Japan.

Optionally, the dormant implant 32 may include other components for carrying out a variety of monitoring, diagnostic, and/or therapeutic functions. For example, the electrical circuit 34 may include a control circuit, memory, a biosensor, an actuator, and/or a transmitter (none of which are shown), as explained in more detail below. The dormant implant 32 may be configured for providing one or more therapeutic functions, for example, to activate and/or control a therapeutic device implanted within a patient's body, such as an atrial defibrillator, a pacemaker, a pain relief stimulator, a neuro-stimulator, a drug delivery device (e.g., an insulin pump), and/or a light source used for photodynamic therapy. Alternatively, the implant 32 may be used to monitor a radiation dose including ionizing, magnetic and/or acoustic radiation, to monitor flow in a bypass graft, to produce cell oxygenation and membrane electroporation, and the like. In addition or alternatively, the implant 32 may include one or more sensors for measuring one or more physiological parameters within the patient's body, such as pressure, temperature, electrical impedance, position, strain, fluid flow, pH, and the like.

For example, the implant 32 may include a biosensor including one or more sensors capable of measuring physiological parameters, such as those described above. U.S. Pat. No. 4,793,825 issued to Benjamin et al. and U.S. Pat. No. 5,833,603 issued to Kovacs et al., which disclose exemplary embodiments of biosensors that may be included in an implant, in accordance with the present invention. The disclosure of these references and any others cited therein are expressly incorporated herein by reference. The biosensor may generate a signal proportional to a physiological parameter that may be processed and/or relayed by the electrical circuitry 34 to the acoustic transducer 36, which, in turn, may generate a transmission signal to be received by the control implant 12.

In addition or alternatively, the implant 32 may include an actuator (not shown) that may be coupled to a therapeutic device (also not shown) provided in or otherwise coupled to the implant 32, such as a light source, a nerve stimulator, a defibrillator, or a valve communicating with an implanted drug reservoir (in the implant or otherwise implanted within the body in association with the implant). For example, the actuator may be a light source for photo-dynamic therapy, such as that disclosed in U.S. Pat. No. 5,800,478 issued to Chen et al., the disclosure of which is expressly incorporated herein by reference.

Thus, the second implant 32 may remain in a dormant state and become active upon receiving an acoustic signal that may induce a voltage high enough to close the acoustic switch 42. In the dormant state, the second implant 32 may consume substantially little or no energy, thereby allowing it to remain within the body substantially indefinitely.

Once activated, the acoustic transducer 36 may convert the acoustic signals received, e.g., from the control implant 12, into one or more electrical signals, which may be processed by the electrical circuitry 34 or otherwise used to control operation of the dormant implant 32. The acoustic transducer 36 may also be used to charge the energy source 38, e.g., a rechargeable battery and/or capacitor. Similar to the control implant 12 described above, the acoustic transducer 36 may include one or more piezoelectric elements that may be used to receive acoustic signals, to transmit acoustic signals, or both.

Figure 4:
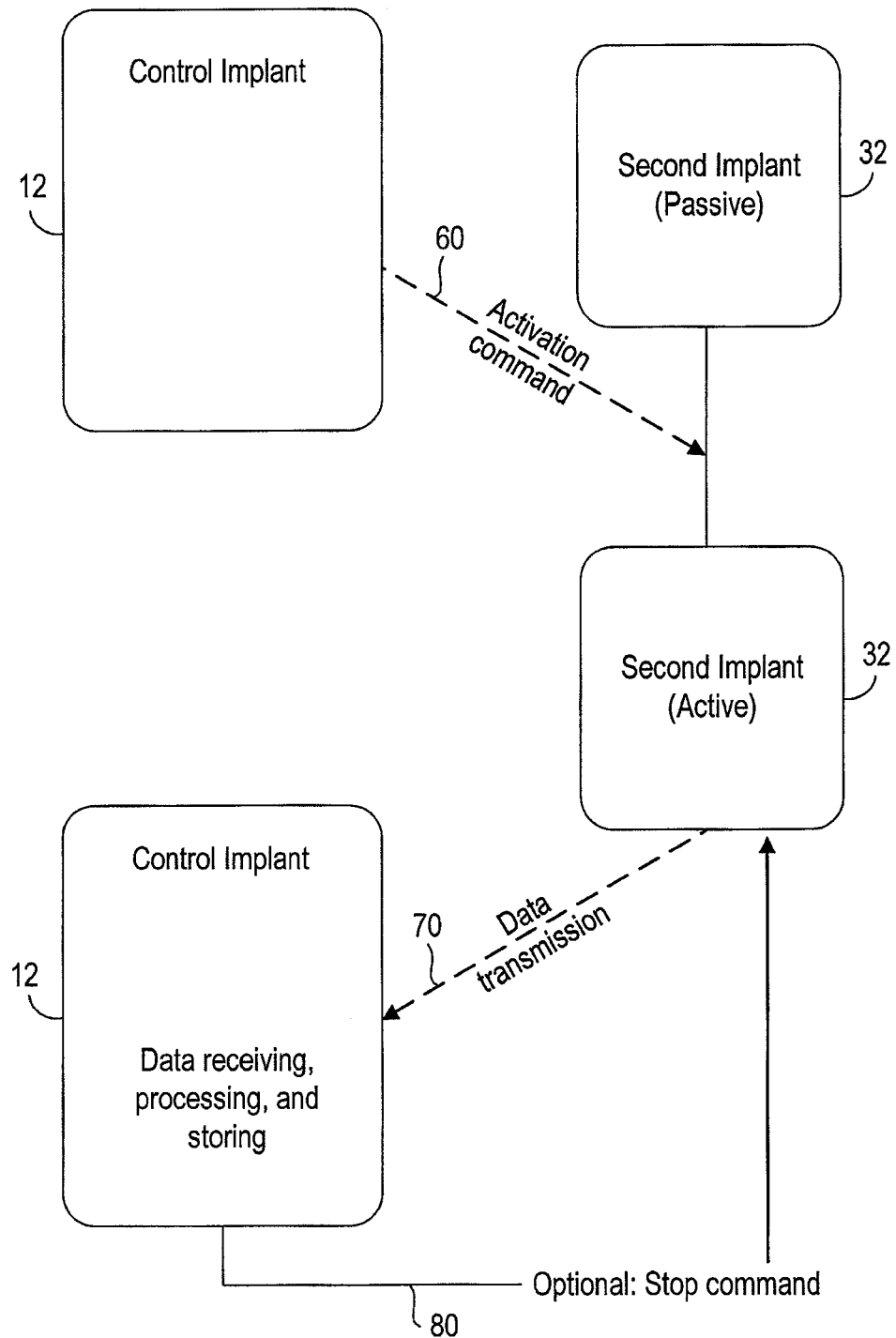
FIG. 4 is a flow diagram, showing an exemplary sequence of communications between master and slave implants, in accordance with the present invention.

FIG. 4 shows an exemplary sequence of operations that may be performed by a system, such as the system 10 shown in FIG. 1. Initially, the control implant 12 and second implant 32 may be implanted within the patient's body at different locations, with the second implant 32 being in a passive or "sleep" mode. At step 60, the acoustic transducer 16 of the control implant 12 may transmit one or more acoustic signals, including an activation command, that may be received by the acoustic transducer 36 of the second implant 32. If the acoustic signal(s) satisfy the threshold requirements of the acoustic switch 42, the switch 44 may be closed, thereby activating the second implant 32.

For example, the acoustic switch 42 may only be activated when it receives a specific sequence of acoustic signals, e.g., an initiation pulse followed after a predetermined delay by a confirmation pulse. Such a sequence may prevent false activation/deactivation and/or may be used to activate only one of multiple dormant implants (not shown), e.g., by assigning different threshold parameters to each of the dormant implants. Using a confirmation signal may be particularly important for certain applications, for example, to prevent unintentional release of drugs by a drug delivery implant. In addition, the initiation signal and/or confirmation signals may be unique, i.e., configured to activate a single selected dormant implant 132, e.g., if multiple dormant implants 32 are implanted within the patient's body 90.

Once the second implant 32 is activated, the acoustic transducer 36 may convert the acoustic signal(s) into one or more electrical signals, and the electrical circuitry 34 of the second implant 32 may analyze the electrical signal(s). For example, the electrical circuitry 34 may extract one or more commands from the signal(s), and then control the implant 32 to complete the command(s). Alternatively, the second implant 32 may be preprogrammed, and may automatically perform a predetermined sequence of operations once activated. This may involve activating one or more sensors to obtain physiological data related to the patient, and/or actuating a therapeutic and/or diagnostic device (not shown) coupled to the second implant 32.

At step 70, the acoustic transducer 36 of the second implant 32 may transmit one or more acoustic signals including data back to the control implant 12. This may involve associating physiological data obtained from one or more sensors with respective time stamps, and converting the data to signals that may be transmitted by the acoustic transducer 36. In addition, the acoustic signal(s) may include operating parameters of the second implant 32 and/or a device (not shown) coupled to the second implant 32. The acoustic transducer 16 of the control implant 12 may receive the acoustic signal(s) and convert the acoustic signal(s) into one or more electrical signals from which the electrical circuitry 14 of the control implant 12 may extract physiological data or other information generated by the second implant 32. The control implant 12 may store the data, e.g., for later retrieval and/or transmission to an external recorder and/or controller. In addition, the control implant 12 may use the data to control another implant (not shown) that may be coupled directly, e.g., via one or more leads, or indirectly, e.g., via acoustic telemetry, to the control implant 12. For example, the control implant 12 may interrogate the second implant 32 to obtain data related to physiological parameters of the patient, and then control another implanted device, e.g., a pacemaker or insulin pump, to operate in a particular manner.

If the second implant 32 is configured to operate continuously and/or indefinitely, at step 80, the control implant 12 may transmit one or more acoustic signals to deactivate the second implant 32 after it has obtained sufficient data. Similar to the activation signal(s) described, the deactivation signal(s) may include an initiation pulse followed by a confirmation pulse or other sequences necessary to ensure the appropriate implant responds appropriately. Once the deactivation signal is received by the second implant 32, the switch 44 may open, returning the second implant 32 to its sleep mode. Alternatively, the implant 132 may include a timer (not shown), such that the switch 44 remains closed only for a predetermined time, e.g., monitoring pressure continuously or intermittently when activated, whereupon the switch 44 may automatically open, returning the implant 132 to its sleep mode.

III. Exemplary Embodiments

A. Measuring Physiological Pressure

In one embodiment, a dormant implant, such as the implant 32 shown in FIG. 1, may be used to monitor physiological pressure at a location within a patient's body where the dormant implant 32 is implanted. For such an application, the dormant implant 32 may include a pressure sensor (not shown) coupled to the electrical circuitry 34. The pressure sensor may be contained within the implant 32, i.e., with an active sensor probe exposed to pressure within the patient's body, although, alternatively, the pressure sensor may be coupled to the implant 32, e.g., by one or more leads (in either case, this pressure sensor may be referred to herein as the "internal pressure sensor").

Because the internal pressure sensor may measure absolute pressure, it may be necessary to determine the patient's physiological pressure, i.e., a gauge pressure, within the patient's body from this absolute pressure measured. To accomplish this, the patient may carry an "external" pressure sensor (not shown) for measuring ambient barometric pressure. The external pressure sensor may assign and/or store a time stamp with any barometric pressure measured, e.g., uniquely identifying a time, date, and the like when the barometric pressure was measured. The sensor may include a timer and/or memory to facilitate time stamping the barometric pressure data. Alternatively, the dormant implant 32 and/or the control implant 12 may assign a time stamp to barometric pressure data obtained from the external pressure sensor.

For example, the external pressure sensor may be secured to an exterior of the patient's skin, e.g., on a patch adhered to the patient's skin, a belt, or otherwise carried such that it is exposed to ambient pressure outside the patient's body. The control implant 12 and/or the dormant implant 32 may be coupled to the external sensor, e.g., directly via one or more leads, or indirectly, e.g., via a wireless transmitter/receiver, such as an acoustic or RF transducer. The control implant 12 or the dormant implant 32 may assign a time stamp to the barometric pressure data, e.g., using their internal clock(s) and/or may store the barometric pressure data and associated time stamp locally in memory.

The dormant implant 32 may be used to measure absolute internal pressure data using the internal pressure sensor. The dormant implant 32 may assign a time stamp to any internal pressure data, and transmit the time stamp to the control implant 12 along with the associated internal pressure data. The control implant 12 may then subtract the barometric pressure (obtained from the external sensor) from the absolute pressure (obtained from the internal sensor) having the same time stamp to yield the desired physiological pressure at the time identified by the time stamp. The control implant 12 may then store any of the data, e.g., physiological pressure data and/or the other data, locally in memory for later use, and/or may use the data to monitor and/or change treatment parameters related to the patient.

In another embodiment, a barometric pressure sensor (not shown) may be implanted in the patient's body, e.g., subdermally near the control implant 12. The sub-dermal sensor may be coupled to the control implant 12, e.g., directly (via one or more leads, or via a pressure lumen of a catheter configured to transfer pressure) or indirectly (via acoustic telemetry or other wireless communications link), similar to the external sensor described above. Alternatively, if the control implant 12 is implanted subdermally or otherwise close to the skin, a barometric pressure sensor may be included within the control implant 12, e.g., beneath a pressure sensitive area of the casing 20 of the control implant 12. Although a sub-dermal pressure sensor may not provide a precise measure of barometric pressure, it may provide a sufficiently accurate estimate of barometric pressure to allow the physiological pressure to be reasonably estimated. Other apparatus and methods for obtaining barometric pressure data, e.g., using a location finder, are disclosed in co-pending application Ser. No. 10/152,091, filed May 20, 2002, and entitled "Barometric Pressure Correction Based on Remote Sources of Information," and U.S. Pat. No. 6,234,973 issued to Meador et al. The disclosures of these references and any others cited therein are expressly incorporated by reference herein.

In a preferred embodiment, the system 10 may be used to monitor pressure within a patient's cardiovascular system. For example, one of the implants, i.e., the control implant 12 or the dormant implant 32, may be incorporated into and/or coupled to other diagnostic and/or therapeutic devices implanted within the patient's cardiovascular system, e.g., a pacemaker. The other implant may be implanted relatively close to the surface of the patient's body, e.g., subdermally. For example, the control implant 12 may be located subdermally, while the dormant implant 32 may be implanted deeper within the patient's body, e.g., within a blood vessel or adjacent to the patient's heart. For a deeply implanted dormant implant 32, it is preferred that the energy source 38 be a battery having sufficient power to allow the dormant implant 32 to operate intermittently for an extended period of time without requiring recharging or exchange. The acoustic switch 42 may allow the implant 32 to remain dormant, i.e., using little or no electrical energy, for extended periods of time until activated by the control implant 12, thereby minimizing its energy consumption and extending its useful life.

To illustrate the energy requirements of a dormant implant, the energy consumption of a dormant acoustic implant (such as those disclosed in the applications incorporated by reference above), when activated, may be about five microamperes (I~5 µA). The minimal required operation time may be as low as about one (1) second. Assuming three (3) seconds for sampling a few heartbeats (t=3 seconds), and assuming that about ten (10) pressure samples per day may be desired, the total sampling duration, T, over a year would be about three hours (T=3×10×365=$10^4$ seconds~3 hours). This would result in the amount of power being consumed during a year of such pressure measurements to be about fifteen microampere hours ($P_{sampling}$=15 µA Hr).

The leakage current through a properly functioning acoustic switch should be smaller than about one nanoampere (1 nA). Assuming one nanoampere (1 nA) leakage rate, the leakage over a year will be about nine microampere hours ($P_{leakage}$=1 nA×8760 Hr=8.7 µA Hr). Thus, the total power consumed by a dormant implant, including desired activation time and leakage would be about twenty four microampere hours (24 µA Hr).

Batteries are available that may be incorporated into an implant while maintaining the overall implant size not larger than eight millimeters long, two millimeters wide, and 0.3 millimeters thick (8 mm×2 mm×0.3 mm, Length×Width×Thickness). For example, a thin film lithium battery to accommodate this size may have a capacity of about two hundred microampere hours per square centimeter per fifteen micrometer thickness (200 µA Hr $cm^{-2}$/15 µm) thick cell. Assuming ten (10) layers of cells, the overall capacity of such a battery would be about two thousand (2,000) µA Hr $cm_{-2}$. For a battery cell area of about 0.8 cm×0.2 cm, the overall capacity of the battery (assuming fifty percent (50%) cathode efficiency) would be about one hundred sixty microampere hours ($P_{battery}$=0.8×0.2×1000=160 µA Hr).

This suggests that, given the assumption that ten (10) pressure samples are taken per day, the battery life would be more than six years. If the battery is rechargeable, e.g., using acoustic energy transformed using an energy exchanger, such as the acoustic transducer 36 described above (and disclosed in U.S. Pat. No. 6,140,740, the disclosure of which is expressly incorporated herein by reference), this life may be extended further.

Figure 5:
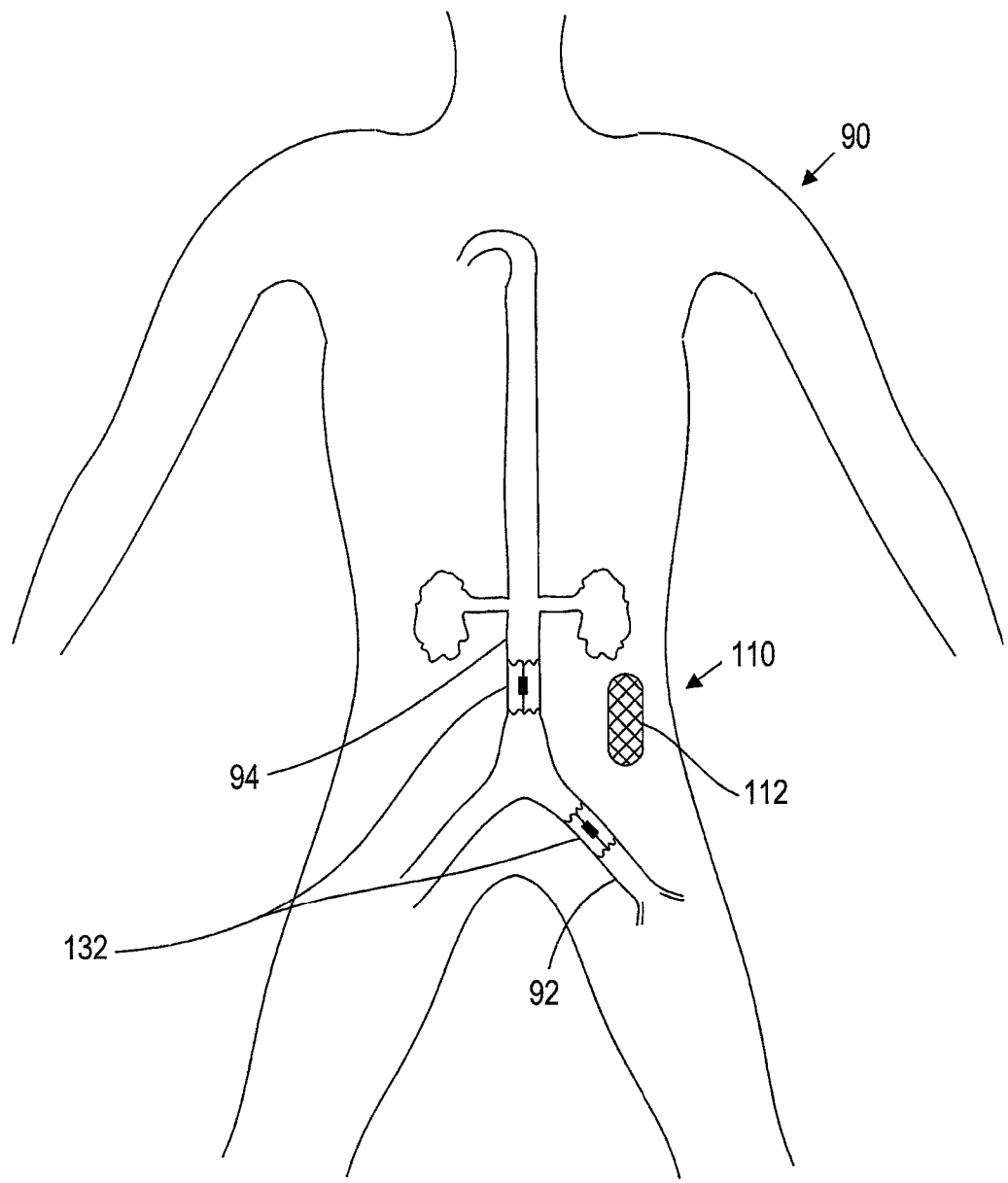
FIG. 5 is a cross-section of a body, showing a system for monitoring blood pressure within the body.

Turning to FIG. 5, an exemplary embodiment of a system 110 is shown that includes a control implant 112 and a plurality of dormant implants 132 for monitoring hypertension within a patient 90. Although two dormant implants 132 are shown, it will be appreciated that one or more implants 132 may be used, depending upon the number of points from which pressure is desired to be measured. The control implant 112 and/or dormant implant(s) 132 may be constructed similar to any of the embodiments described above.

Hypertension is one of the most widespread diseases in the modern world, affecting an estimated fifty million people in the United States alone, and with about one million new cases being diagnosed annually. It is often devoid of symptoms and as many as one third of patients are unaware of their illness. Nevertheless, hypertension is strongly associated with a high risk for stroke, chronic heart failure ("CHF"), myocardial infarction ("MI"), renal failure, and other health problems, and may have a causal relationship with many of these diseases. Direct mortality from hypertension was attributed to about forty two thousand (42,000) in the United States in 1997, and it was a contributing factor in about two hundred ten thousand (210,000) additional deaths.

Blood pressure (BP) regulation is based on a complex neuro-hormonal balance, involving a wide variety of systemic and local regulating hormones and substances that regulate cardiac function, systemic resistance, and renal function. Feedback may be provided by groups of baroreceptors located in the cardiac atrium and in the carotid arteries. Hypertension is defined as a systolic pressure above about one hundred forty millimeters of Mercury (140 mm Hg) and/or a diastolic pressure above about ninety millimeters of mercury (90 mm Hg). Between about ninety and ninety five percent (90-95%) of hypertension is primary. Hypertension is often diagnosed serendipitously during routine BP measurements, but may also produce symptoms such as dizziness, headaches, or vision disturbances. Of the about fifty million Americans estimated to have hypertension, about thirty two percent (32%) are unaware of their condition, about fifteen percent (15%) have mild hypertension and are not medicated, about twenty seven percent (27%) are medicated and their BP is well controlled, while about twenty six percent (26%) are medicated without achieving proper control of the BP.

Treating hypertension is a complex task, and may address several points in the regulation of BP. However, the task is often difficult, and half the patients being treated for hypertension may not achieve proper control of their BP. The lack of control contributes significantly to associated morbidity and mortality, imposing a high cost on the health care system and society at large.

To monitor and/or treat hypertension, a patient's BP may be measured periodically, e.g., generally during office visits with a physician. In some cases, this may be supplemented by home measurements by the patient. However, whether these infrequent measurements are done, the therapy and the measure for the success of the therapy are based on sporadic, random measurements. Monitoring using a BP Holter device, a twenty four (24) hour BP recording device, may be employed to produce a more comprehensive picture of the disease in uncontrolled patients. The device, however, is uncomfortable, cumbersome, and expensive to use, and its clinical application has been limited since it cannot be used on a chronic base.

In contrast, the system 110 of FIG. 5 may allow a patient's BP to be measured frequently over an extended period of time. As shown, each dormant implant 132 may be implanted in an artery, such as the iliac artery 92 or the aorta 94 (which may be more easily accessed, due to their size, with minimal convenience, and/or which may be more easily protected). Within the artery, the dormant implant(s) 132 may monitor the patient's BP periodically, e.g., at a frequency programmed by the patient's physician. For example, the control implant 112 may be programmed at time of implantation to periodically interrogate each dormant implant 132, e.g., several times a day. Alternatively, the control implant 112 may be programmed periodically using an external device (not shown). In this alternative, the control implant 112 may include a receiver, which may be the same acoustic transducer used to transmit acoustic signals to and/or receive acoustic signals from the dormant implant(s) 132. Alternatively, the control implant 112 may include a separate receiver, e.g., a RF or acoustic transmitter/receiver, that may communicate with external devices.

Each dormant implant 132 may be no larger than about nine millimeters in length by two millimeters in width, by one millimeter in thickness (9 mm×2 mm×1 mm, L×W×T). The dormant implant(s) 132 may be implanted endoluminally, for example, using a catheter or sheath, e.g., about seven French (7 Fr.) or smaller, that may be introduced percutaneously into a peripheral artery, e.g., a femoral artery, and advanced to the implantation site using conventional methods.

In one embodiment, the implant 132 may be secured within the artery using a scaffolding structure or other fixture, similar to a stent, to which the implant 132 may be secured.

Exemplary structures that may be used to carry and/or deliver a dormant implant are disclosed in U.S. Pat. No. 6,442,413 or published PCT application No. WO 99/34,731. The disclosures of these references and any others cited therein are expressly incorporated herein by reference. Alternatively, a dormant implant may be attached to a graft structure for detecting endoleaks within an aneurysm, such as those disclosed in co-pending application Ser. No. 09/522,724, filed Mar. 10, 2000, the disclosure of which is expressly incorporated herein by reference. The implant 132 may be implanted in a dedicated procedure, may be implanted in conjunction with another procedure, e.g., a catheterization procedure, such as coronary catheterization or a peripheral intervention, or may be sutured in a vessel in conjunction of another open or minimally invasive surgical or endoscopic procedure, such as coronary bypass.

The control implant 112 may be implanted at a different location than the implantation site(s) of the pressure sensing implant(s), for example, at a sub-dermal location within the patient's abdomen. The location may be accessed via a small superficial incision, e.g., about two centimeters (2 cm) long, to create a pocket within which the control implant 112 may be received.

Once implanted, the control implant 112 may periodically interrogate the dormant implant(s) 132, which may then acquire BP data and transfer the data back to the control implant 132, whereupon the control implant 112 may store the data (preferably along with associated time stamps) within its memory. Optionally, in addition to BP measurements, the system may also acquire and store data related to the patient's exertion, e.g., to correlate the patient's BP to his/her level of exertion at the time. For example, a silicon one accelerometer sensor (not shown) may be provided in the control implant or otherwise carried by the patient to monitor the patient's level of physical activity. In addition or alternatively, the system may determine the patient's posture at the time of obtaining BP data for calculating an orthostatic correction factor.

Occasionally, e.g., at regularly scheduled time, the control implant 112 may be interrogated, e.g., in a clinic, hospital, or other health care facility to receive the BP (and other associated) data to monitor the patient's condition and/or modify their treatment. To obtain the data, an external controller and/or recorder may be provided, similar to that disclosed in the applications incorporated by reference above. The recorder may be placed in contact with the patient's skin, e.g., in close proximity to the control implant 112, and the control implant 112 may be instructed to transmit the BP data, e.g., using acoustic telemetry and the acoustic transducer 116, or using another communication link, e.g., RF telemetry.

Alternatively, a home-based patient monitor, e.g., a controller and/or recorder (not shown), may be used that may interrogate the control implant 112 transfer the BP data, e.g., over telephone, internet, or other telecommunications systems, to a health care facility for evaluation. Optionally, the external controller may be used to change the frequency and/or other parameters of the activities performed by the control implant 112 and/or dormant implants 132. For example, the external controller may transmit new parameters to the control implant 112, which may store them for future activity and/or relay them to any dormant implants 132 with which it communicates.

The BP data transmitted by the control implant 112 may include full pressure patterns or simply one or more desired parameters, such as systolic, diastolic, and/or mean blood pressure. The collected data may give a comprehensive picture of the patient's disease and its management, may optimize drug treatment of the patient, and/or may allow efficient treatment for currently uncontrolled patients. It may also reduce the frequency of office visits and hospitalizations, thereby reduce the cost of treating the patient.

B. Heart Pressure Monitoring

In another embodiment, the systems and methods of the present invention may be used for monitoring pressure with heart chambers and/or great vessels within a patient's heart. The data obtained may be used to provide physiological feedback to a device, e.g., for a pacing implant, such as a pacemaker or bi-ventricle pacer, in order to optimize the performance to the device.

For example, a bi-ventricular pacemaker (not shown) may control a delay between the contractions of different chambers of a patient's heart, e.g., to optimize the pumping efficiency of the heart. A dormant transducer may act as a telemetric pressure sensor, transmitting pressure data from a vessel, e.g., pulmonary artery, left atrium, or left ventricle, to the bi-ventricular pacemaker for providing feedback to the pacemaker. A dormant implant may also be used to measure pressure and transfer pressure data to improve the performance of a defibrillator.

An implantable cardioverter defibrillator (ICD) is a device that may be implanted in the chest to monitor for and, if necessary, correct episodes of rapid heartbeat. If the heartbeat gets too fast (ventricular tachycardia), the ICD may stimulate the heart electrically to restore a normal rhythm (antitachycardia pacing). In cases where the heartbeat is so rapid that the person may die (ventricular fibrillation), the ICD may also give an electric shock (defibrillation) to "reset" the heartbeat.

To facilitate deciding what mode for the ICD to use, systems and methods in accordance with the present invention may be used to monitor pressure within the heart chambers in order to differentiate between conditions, e.g., whether a patient is experiencing atrial fibrillation or ventricular fibrillation. For example, a system similar to those described above may be provided that includes one or more dormant implants implanted in the left ventricle, the left atrium, and/or the pulmonary artery of the patient. A control implant may be implanted subcutaneously, e.g., by creating a small superficial incision, e.g., about two or three centimeters (2-3 cm) long, in the chest within which the control implant may be inserted, whereupon a few sutures may be used to close the incision. The control implant may be coupled to an ICD, e.g., directly or indirectly, similar to the embodiments described above. Alternatively, the components of the control implant may be incorporated into an ICD.

During use, the control implant may activate one or more dormant implants that may measure pressure in the respective cardiac region(s), and transmit the information to the control implant. This may involve activating multiple dormant implants alternately, sequentially, and/or simultaneously, receiving pressure data and storing the data in memory of the control implant, similar to the embodiments described previously. A health care profession and/or the patient may periodically download the pressure data using an external device communicating using acoustic or RF telemetry, also similar to the embodiments described above. The readings may enable the physician to make a decision about the adequacy of the medical treatment the patient receives, and make the appropriate corrections, if required, e.g., by reprogramming the patient's ICD, control implant, and/or dormant implant(s). This in turn, may ensure better patient treatment, better use of the medical resources, and reduce the need for hospitalization.

Alternatively, the system may allow an ICD to automatically determine whether merely to stimulate or to defibrillate, since these two types of fibrillation require different treatments. One or more dormant implants may be provided within different chambers of the patient's heart, e.g., for monitoring pressure therein. A control implant may be provided outside the heart, e.g., coupled to or provided within a pacemaker, that may selectively or periodically interrogate the dormant implant(s) to obtain pressure data. The data may then allow the control implant and/or pacemaker to determine the appropriate response to the patient's condition.

Alternatively, the systems and methods of the present invention may be used to provide hemodynamic feedback for a congestive heart failure (CHF) patient. Hemodynamic information, and more specifically pressure information, may be used to improve treating CHF patients. CHF is a complex chronic and progressive disease, in which the capacity of the heart to pump is compromised, and the ability of the patient to perform physical activity is reduced. The body employs a variety of compensatory mechanisms to offset the pumping failure, which becomes symptomatic when their compensatory capacity is exceeded. The overall prognosis for patients diagnosed with heart failure is one of a gradual deterioration of cardiac function, eventually leading to death.

Managing CHF is a complex task, and involves balancing several drugs, which may interact with each other and/or trigger further compensatory responses. Thus, treating CHF is an art of balancing the hemodynamic status of the patient in a state of compensation in order to slow progression of the disease. The delicate balance of compensation may be easily upset, resulting in decompensation crises. Current monitoring techniques may not prevent these episodes, which account for about one million hospitalizations every year in the United States, totaling about six and a half million hospital days a year.

C. Providing a Feedback Loop for Insulin Dosing

Diabetes is the sixth leading cause of death in the United States and is rapidly increasing in prevalence. For millions of diabetics who cannot be treated by dietary changes alone, successful control of their disease depends upon adequately monitoring and treating blood sugar levels with insulin. To do so, diabetics must repeatedly stick their fingers with needles and submit blood samples to a blood sugar or glucose test. Depending upon the result, they must then inject themselves with a dose of insulin to bring their glucose back to an acceptable level. Failure to maintain the appropriate blood sugar level may lead to serious complications involving multiple body organs and progression of cardiovascular and kidney disease, vision impairment, and/or peripheral vascular disease.

Even with these incentives to maintain appropriate glucose control, many patients consider the endless cycle of fingersticks and insulin injections to be burdensome. In addition, for maximum effectiveness, insulin should be administered as closely as possible to the time when it is needed. This time, however, may occur at an inconvenient moment, e.g., in the middle of a meal or in a social environment where there may be stigma associated with syringes or other devices used to deliver insulin. Thus, a diabetic may often compromise proper glucose control for convenience, social conformity, and/or quality of life. Too often, these actions lead to less than optimal blood sugar control, diminished outcomes for diabetics, and increased hospitalization costs.

Even a model diabetic patient who does not miss a blood sugar measurement or insulin injection, however, cannot monitor glucose with the level of precision obtained by the body's natural insulin producer, the pancreas. For diabetics, the most important function of the pancreas is to produce the hormone insulin. A properly functioning pancreas continuously monitors blood sugar levels and responds by releasing insulin to assist the body in using its glucose. Although it is possible to transplant a human pancreas, the rejection rate is high and there are limited numbers of donors available. Thus, much attention is focused on finding an "artificial pancreas" alternative.

Artificial pancreas research attempts to produce a pump-like device that may continuously monitor glucose levels and immediately respond by delivering precise insulin doses needed at any given moment, just as the human pancreas does naturally. Insulin pumps are already available, for example, from companies such as Mini Med (CA). There are currently two types of insulin pumps available, a fully implanted pump that is implanted within a patient's abdomen, and an external pump that injects insulin through a needle subcutaneously. Exemplary insulin pumps are disclosed in U.S. Pat. Nos. 4,373,527 and 4,573,994, and in published European Patent Application No. EP 300,552, the disclosures of which are expressly incorporated herein by reference.

Figure 6:
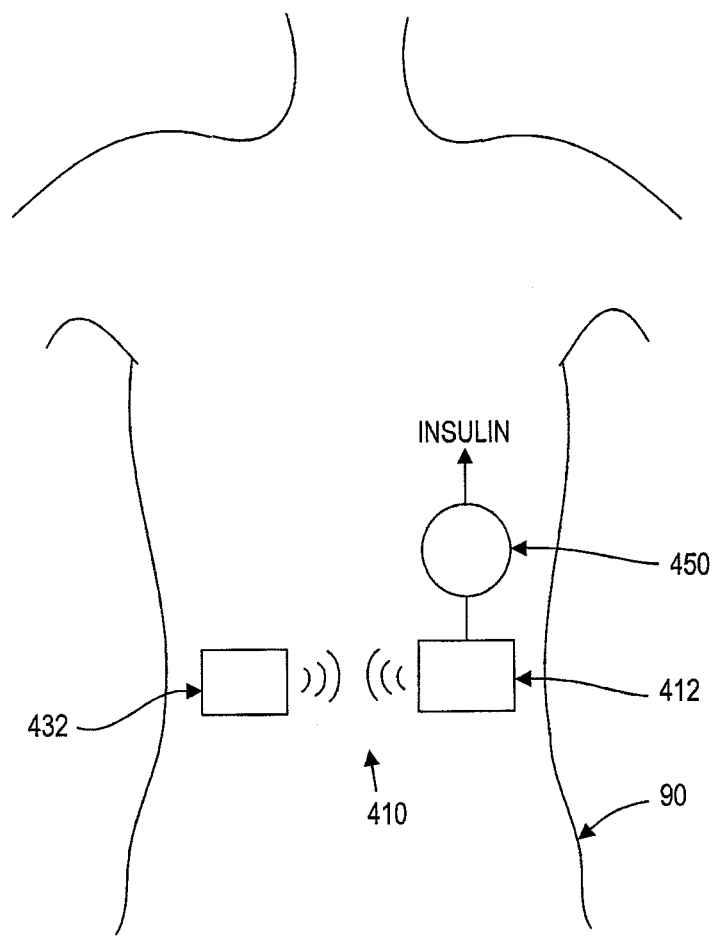
FIG. 6 is a cross-section of a body, showing a closed loop system for delivering insulin within the body.

Turning to FIG. 6, a system 410 is shown that includes a control implant 412 and a glucose sensor 432 that may be implanted within a patient's body 90 to provide feedback to an insulin pump 450. As explained above, the insulin pump 450 may be fully implanted within the body 90 or may be external the body 90 with a needle (not shown) extending from the pump into the patient's body. If the insulin pump 450 is implanted, the control implant 412 may be coupled directly to the insulin pump 450, e.g., via one or more leads, or indirectly, e.g., via wireless telemetry. Alternatively, the components of the control implant 412 may be incorporated directly into the insulin pump 450, which may then be implanted at a desired location within the patient's body.

The control implant 412 may include one or more components, similar to the control implants described above, e.g., an acoustic transducer, electrical circuitry, memory, and/or an energy source (not shown). The glucose sensor 432 may be a dormant implant similar to the embodiments described previously, including an acoustic switch, an acoustic transducer, an energy source, electrical circuitry, and/or a sensor for measuring blood sugar concentration (not shown). The glucose sensor 432 may be implanted at any location allowing it to measure the patient's glucose concentration. Preferably, because the service life of a glucose sensor may be relatively short, e.g., currently only days (and possibly lasting weeks or months in the future), the glucose sensor 432 may be implanted subcutaneously, e.g., within the patient's abdomen, or at another location that may be accessed relatively easily. Thus, all or part of the glucose sensor 432 may be replaced, after its service life has expired, with a new glucose sensor (not shown) that may continue to provide feedback to the control implant 432 and/or insulin pump 450.

Thus, the system 410 may provide a closed loop, allowing frequent feedback to control a rate of insulin delivered by the insulin pump 450, and thereby preventing substantial fluctuations of the patient's blood sugar concentration. An acoustic transducer (not shown) of the control implant 412 may periodically interrogate the glucose sensor 432, whereupon the glucose sensor 432 may measure the patient's blood sugar concentration and transmit data back to the control implant 412 via its acoustic transducer (also not shown). The control implant 412 may control the rate of insulin delivery by the pump 450 in response to the data obtained from the glucose sensor 432. Because of the dormant state of the glucose sensor 432, relatively low amounts of energy may be consumed by the glucose sensor 432, which may extend the life of the components of the system 410 substantially, as compared to systems using other modes of communication, such as RF telemetry. Thus, acoustic telemetry may provide a more efficient and convenient method for transferring blood sugar concentration data from the glucose sensor 432 to the insulin pump 450 via the control implant 412.

It will be appreciated that the above descriptions are intended only to serve as examples, and that many other embodiments are possible within the spirit and the scope of the present invention.

We claim:

1. A system for communicating within a patient's body, comprising:
   at least one implantable sensor adapted to be placed within a blood vessel of a patient, the at least one implantable sensor including an electrical energy source and an acoustic transducer configured for acoustic communication with a receiver, wherein the at least one implantable sensor further includes an acoustic switch circuit that is configured to activate the at least one implantable sensor in response to receiving an acoustic signal from an acoustic energy source, wherein the acoustic signal causes the acoustic transducer to form a voltage pulse that is conveyed to the acoustic switch circuit, and wherein the acoustic switch circuit closes, when the voltage pulse exceeds a threshold, to allow current to flow from the electrical energy source, thereby activating the at least one implantable sensor;
   a control implant adapted to be implanted in the patient, the control implant including an acoustic transducer configured for acoustic communication with the at least one implantable sensor; and
   wherein the at least one implantable sensor is coupled to a fixation element adapted to secure the sensor within the blood vessel.

2. The system of claim 1, wherein the at least one implantable sensor includes an actuator.

3. The system of claim 1, wherein the at least one implantable sensor includes one or more sensors each adapted to measure a physiological parameter within the body.

4. The system of claim 3, wherein the one or more sensors includes a pressure sensor.

5. The system of claim 1, wherein the receiver is an external receiver located outside of the body.

6. The system of claim 1, wherein the control implant further includes a transmitter and/or receiver for communicating with one or more external devices in communication with the control implant.

7. The system of claim 1, wherein the acoustic energy source is the control implant.

8. The system of claim 1, wherein the acoustic energy source is an external device.

9. The system of claim 1, wherein the fixation element is a stent.

10. The system of claim 1, wherein the acoustic transducer for the control implant is coupled to a lead.

11. The system of claim 1, wherein the acoustic transducer for the control implant is coupled to a control housing of the control implant.

12. A system for communicating within a patient's body, comprising:
    at least one implantable sensor adapted to be placed within a blood vessel of a patient, the at least one implantable sensor including an electrical energy source, electrical circuitry configured to control an operation of the at least one implantable sensor, and an acoustic transducer configured for acoustic communication with a receiver, wherein the at least one implantable sensor further includes an acoustic switch that is configured to allow an electrical current to flow from the energy source to the electrical circuitry in response to receiving an acoustic signal, thereby activating the at least one implantable sensor; and
    a control implant adapted to be implanted in the patient, the control implant including an acoustic transducer configured for acoustic communication with the at least one implantable sensor.

* * * * *